(12) United States Patent
Marshall et al.

(10) Patent No.: US 7,191,016 B2
(45) Date of Patent: Mar. 13, 2007

(54) MEDICAL SYSTEM INCLUDING A NOVEL BIPOLAR PACING AND SENSING PAIR

(75) Inventors: Mark T. Marshall, Forest Lake, MN (US); Teresa A. Whitman, Dayton, MN (US); Eduardo N. Warman, Maple Grove, MN (US); Jeffrey M. Gillberg, Coon Rapids, MN (US); Matthew D. Bonner, Plymouth, MN (US); Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 567 days.

(21) Appl. No.: 10/439,201

(22) Filed: May 15, 2003

(65) Prior Publication Data

US 2004/0230275 A1 Nov. 18, 2004

(51) Int. Cl.
*A61N 1/05* (2006.01)
(52) U.S. Cl. .................................... 607/122
(58) Field of Classification Search ............... 607/48, 607/122
See application file for complete search history.

(56) References Cited

U.S. PATENT DOCUMENTS

| | | | | |
|---|---|---|---|---|
| 4,365,639 A | 12/1982 | Goldreyer | ................ | 128/786 |
| 4,762,136 A | 8/1988 | Baker, Jr. | ................ | 128/786 |
| 4,922,927 A | 5/1990 | Fine et al. | ................ | 128/786 |
| 5,052,407 A | 10/1991 | Hauser et al. | ................ | 128/786 |
| 5,090,422 A | 2/1992 | Dahl et al. | ................ | 128/784 |
| 5,269,810 A * | 12/1993 | Hull et al. | ................ | 607/129 |
| 5,374,287 A | 12/1994 | Rubin | ................ | 607/131 |
| 5,385,146 A | 1/1995 | Goldreyer | ................ | 128/642 |
| 5,450,846 A | 9/1995 | Goldreyer | ................ | 128/642 |
| 5,466,252 A * | 11/1995 | Soukup et al. | ................ | 607/116 |
| 5,579,764 A | 12/1996 | Goldreyer | ................ | 128/642 |
| 5,824,029 A * | 10/1998 | Weijand et al. | ................ | 607/122 |
| 5,931,862 A * | 8/1999 | Carson | ................ | 607/120 |
| 6,327,498 B1 * | 12/2001 | Kroll | ................ | 607/4 |
| 6,370,434 B1 | 4/2002 | Zhang et al. | ................ | 607/122 |
| 6,405,091 B1 | 6/2002 | Vachon et al. | ................ | 607/120 |
| 2002/0055764 A1 * | 5/2002 | Malonek et al. | ................ | 607/122 |
| 2002/0058981 A1 * | 5/2002 | Zhu et al. | ................ | 607/122 |
| 2002/0193860 A1 * | 12/2002 | Bischoff et al. | ................ | 607/122 |
| 2003/0105501 A1 * | 6/2003 | Warman et al. | ................ | 607/27 |

FOREIGN PATENT DOCUMENTS

WO    WO 02/089909 A1    11/2002

\* cited by examiner

*Primary Examiner*—George Manuel
*Assistant Examiner*—Christopher A. Flory
(74) *Attorney, Agent, or Firm*—Carol F. Barry; Girma Wolde-Michael (57) ABSTRACT

A medical electrical lead includes a first low voltage electrode adapted for intimate contact with tissue at an implant site, in order to provide pacing stimulation, and a second low voltage electrode positioned in proximity to the first electrode, isolated from the first electrode and adapted to function in conjunction with the first electrode to provide bipolar sensing of near-field signals. A porous layer is formed over the second electrode; the porous layer allows conduction therethrough while preventing contact between the second electrode and tissue in proximity to the implant site.

25 Claims, 6 Drawing Sheets

MEDICAL SYSTEM INCLUDING A NOVEL BIPOLAR PACING AND SENSING PAIR

FIELD OF THE INVENTION

Embodiments of the present invention generally relate to the field of cardiac pacing and/or defibrillation, and more particularly to enhanced sensing of near-field cardiac conduction signals.

BACKGROUND

In the field of cardiac pacing and/or defibrillation, therapy delivery from an implanted medical device typically relies upon cardiac signals sensed via a bipolar pair of implanted electrodes included on a medical electrical lead, which is coupled to the medical device. Accurate detection and classification of arrhythmias relies upon an adequate signal-to-noise ratio picked up by the bipolar pair of electrodes; the signal being a near-field cardiac conduction signal and the noise being either a far-field cardiac conduction signal or electrical activity in other muscles of the body or a combination thereof. Many medical devices incorporate sensing algorithms to blank or ignore far-field signals, however this may lead to under-sensing or under-detection of fast regular rhythms. As an alternative, a spacing between the bipolar pair of electrodes on the lead may be decreased in order reduce and localize the field of sensing between the two electrodes.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description. The present invention will hereinafter be described in conjunction with the appended drawings, wherein like numerals and letters denote like elements, and.

DETAILED DESCRIPTION OF EMBODIMENTS OF THE INVENTION

Figure 1:
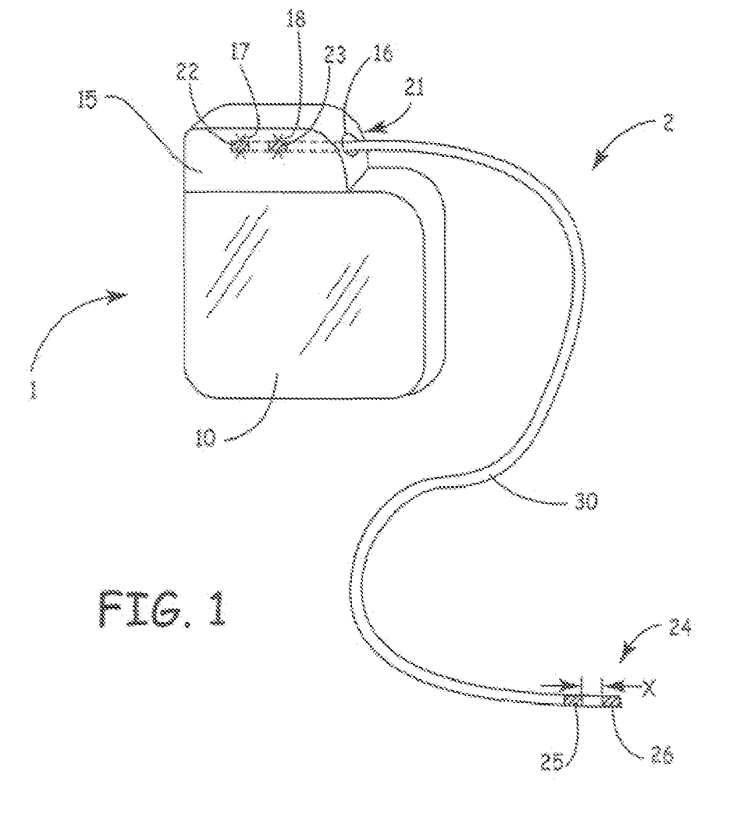
FIG. 1 is a schematic of a medical system according to one embodiment of the present invention.

FIG. 1 is a schematic of a medical system according to one embodiment of the present invention. FIG. 1 illustrates the medical system including an implantable medical electrical lead 2 coupled an implantable medical device (IMD) 1 via a connector header 15; connector header 15 includes a bore 16 to receive a connector formed at a proximal end 21 of lead 2 wherein electrical contacts 17 and 18 of header 15 couple with lead contacts 22 and 23 of connector, respectively. Header 15 is attached to a hermetically sealed enclosure 10 that contains a battery, electronic circuitry and other components known to those skilled in the art, and electrical contacts 17 and 18 are any type known to those skilled in the art that are electrically connected via feedthroughs (not shown) mounted to extend through hermetically sealed enclosure 10 in order to electrically couple lead 2 with IMD 1.

FIG. 1 further illustrates lead 2 including first electrode 26 joined to a lead body 30 in proximity to a distal end 24 and a second electrode 25 joined to lead body 30 in proximity to first electrode 26 and spaced a distance X from first electrode 26. First electrode 26 and second electrode 25 are electrically coupled to lead contacts 22 and 23 via insulated conductors (not shown) extending along lead body 30. According to embodiments of the present invention, first electrode 26 and second electrode 25 form a bipolar pair, each having a surface area adapted for low voltage pacing and sensing, and distance X between first electrode 26 and second electrode 25 is less than approximately 9 millimeters; furthermore, first electrode 26 has a negative polarity and is adapted for intimate contact with tissue at an implant site and second electrode 25 has a positive polarity and is prevented from having direct touching contact with tissue adjacent to the implant site by a porous layer (FIGS. 2–3) formed over second electrode 25. Electrodes 25 and 26, and other electrodes described herein, according to some embodiments, are comprised of a platinum-iridium alloy. First electrode 26, and other first electrodes described herein, may have a porous surface structure enhancing intimate tissue contact as well as a steroid coating formed thereover or a plug comprising steroid formed therein. Details associated with electrode fabrication and alternate electrode materials, including, but not limited to titanium, tantalum, ruthenium, and carbon, are well known to those skilled in the art of lead construction. It should be noted that positions of first electrode 26 and second electrode 25 might be switched according to alternate embodiments of the present invention.

Figure 2A:
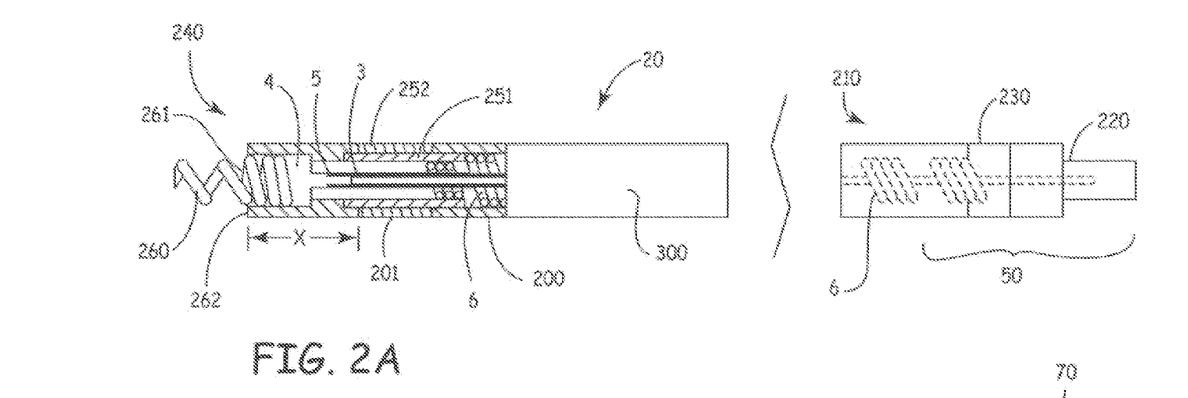
FIG. 2A is a plan view of a medical electrical lead according to one embodiment of the present invention.

FIG. 2A is a plan view including a cut-away section of a medical electrical lead 20 according to one embodiment of the present invention, which may be coupled to an IMD just as lead 2 is coupled to IMD 1 illustrated in FIG. 1. Examples of IMD's suitable for operation in accordance with embodiments of the present invention include, but are not limited to the following Medtronic products: GEM, Marquis DR, Jewel AF, AT 500, and Kappa 900.

FIG. 2A illustrates a body 300 of lead 20 including a distal end 240 and a connector 50 formed at a proximal end 210; a first electrode 260, joined to distal end 240, is coupled to a first contact 220 of connector 50 via a cable conductor 3 extending within insulating sheath 5, and a second electrode 251, joined to lead body 300 in proximity to first electrode 260 and having a porous layer 252 formed thereover, is coupled to a second contact 230 via a coil conductor 6.

Coupling of conductors 3 and 6 to first electrode 260 and second electrode 251 and to first contact 220 and second contact 230 may be accomplished by means of welds or crimps known to those skilled in the art; FIG. 2A illustrates cable conductor 3 coupled to first electrode 260 via a coupling component 4 wherein cable may be crimped and electrode 260 may be welded.

Figure 2B:
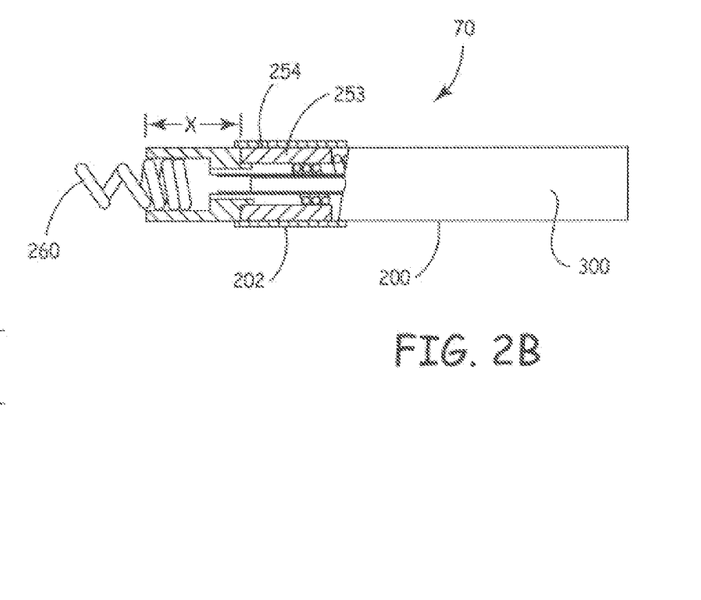
FIG. 2B is a plan view of a distal portion of a medical electrical lead according to another embodiment of the present invention.

According to embodiments of the present invention, a bipolar pair for pacing and sensing is formed by first electrode 260 functioning as a cathode and second electrode 251 functioning as an anode; layer 252 over second electrode 251 allows conduction therethrough while preventing direct touching contact of electrode 251 with tissue adjacent to an implant site, into which electrode 260 would be fixed. FIG. 2A further illustrates first electrode 260 formed as a helix for fixation to the implant site, however, according to other embodiments a first electrode may be formed around or within a fixation helix for example along a surface 262 circumscribing helix or on a surface 261 formed in center of helix wherein fixation of helix into an implant site will bring surfaces 261, 262 into intimate contact with tissue at the implant site. According to one embodiment, second electrode 251 is recessed so that an outer surface 201 of layer 252 is isodiametric with an outer surface 200 of lead body 300, as illustrated in FIG. 2A. FIG. 2B is a plan view including a cut-away section of a distal portion of a lead 70 illustrating an alternate embodiment wherein an outer surface 202 of a porous layer 254 formed over a second electrode 253 has a diameter greater than outer surface 200 of lead body 300.

Figure 2C:
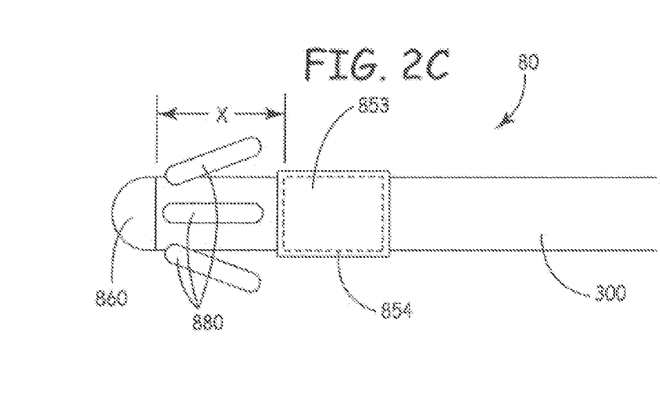
FIG. 2C is a plan view of a distal portion of a medical electrical lead according to yet another embodiment of the present invention.

FIG. 2C is a plan view of a distal portion of a lead 80 according to yet another embodiment of the present invention. FIG. 2C illustrates a first electrode 860 formed as a generally hemispherical dome and a second electrode 853 (shown by dashed lines) joined to lead body 300 in proximity to first electrode 860 and having a porous layer 854 formed thereover. FIG. 2C further illustrates a tine structure 880 formed about first electrode 860 in order to maintain intimate contact of first electrode 860 with tissue at an implant site.

Figure 3A:
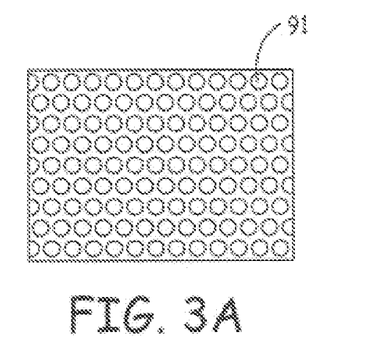
FIGS. 3A–C are enlarged schematic plan views of portions of porous layers according to alternate embodiments of the present invention.
Figure 3B:
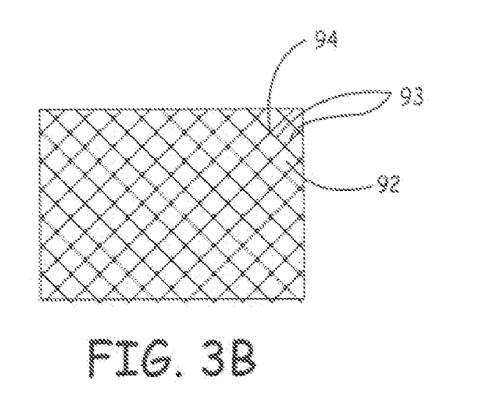
Figure 3C:
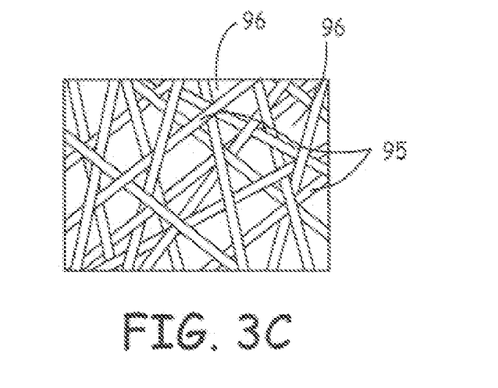

According to embodiments of the present invention a maximum thickness of a porous layer covering a sensing anode, such as layers 252, 254, 854, is between approximately 0.005 inch and approximately 0.020 inch, and pore sizes of the layer, on average are between approximately 0.4 micron and approximately 50 microns. FIGS. 3A–C are enlarged schematic plan views of portions of various porous layers according to alternate embodiments of the present invention. FIGS. 3A and 3B illustrates pores 91 and 92, respectively formed in a substantially uniform pattern, while FIG. 3C illustrates pores 95 formed in a substantially random manner. According to one embodiment of the present invention a porous layer may be formed of a polymer, such as silicone or polyurethane, wherein pores, e.g. 91, are holes formed by mechanical means, e.g. drilling, or thermal means, e.g. laser perforation, as generally illustrated in FIG. 3A. According to an alternate embodiment of the present invention, a porous layer may be formed of a polymer material having a porous microstructure such as expanded polytetrafluoroethylene (e-PTFE), as is generally illustrated in FIG. 3B wherein pores 92 are formed by a network of fibrils 93 connected at nodes 94. Furthermore, an alternate embodiment of a porous layer may employ a sheet of collagen as illustrated in FIG. 3C, wherein pores 95 are formed by a network of collagen fibers 96. FIGS. 3A–C present exemplary porous layers; according to the present invention any type of porous material, which is biocompatible and physically separates a low voltage sensing anode (e.g. second electrodes 251, 253, 853), of a bipolar pair, from tissue in proximity to an implant site while allowing adequate electrical conduction therethrough is in accordance with the spirit of the present invention. In a subset of embodiments a porous layer includes pore sizes, on average, ranging between approximately 0.4 microns and approximately 20 microns in order to prevent chronic tissue ingrowth. Some embodiments of the present invention wherein a porous layer is hydrophobic, e.g. e-PTFE, include a wetting agent impregnated within or spread over the porous layer in order to facilitate passage of fluid through the porous layer necessary for electrical conduction. Examples of wetting agents include surfactants, hydrogels, gelatins or combinations thereof; the use of two surfactants, sodium dioctyl sulfosuccinate (DSS) and tridodecylmethylammonium chloride (TDMAC), in conjunction with e-PTFE is taught by Carson in U.S. Pat. No. 5,931,862, the teachings from which are incorporated herein. Alternate embodiments employ porous layers, surfaces of which are treated to enhance wettability; examples of treatments include but are not limited to plasma processes.

Figure 4A:
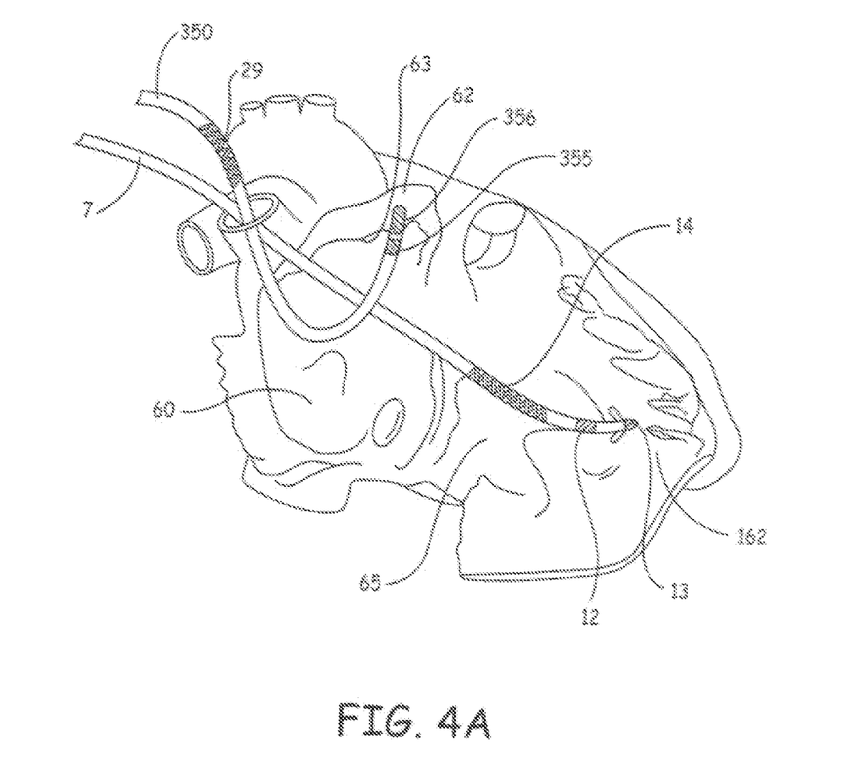
FIG. 4A is a schematic of a lead system implanted within a right side of a heart according to one embodiment of the present invention.

FIG. 4A is a schematic of a lead system implanted within a right side of a heart according to one embodiment of the present invention. FIG. 4A illustrates an atrial lead 350 implanted within an atrium 60 by means of a first electrode 356 fixed to an atrial appendage implant site 62, and a ventricular lead 7 implanted within a ventricle 65 with a tip electrode 13 at an apical implant site 162. According to embodiments of the present invention, leads 350 and 7 are coupled to an IMD, such as any of the aforementioned exemplary IMD's, to form a dual chamber system wherein a second electrode 355 of atrial lead 350, positioned in close proximity to first electrode 356, for example spaced a distance X (FIGS. 1 and 2) from first electrode 356, includes a porous layer formed thereover (FIGS. 2 and 3) to prevent direct touching contact with cardiac tissue along wall 63 adjacent to implant site 62. First electrode 356 and second electrode 355 form a bipolar pair, first electrode 356 being a cathode and second electrode 355 being an anode, for pacing and sensing, wherein sensing of near field cardiac signals, or P-waves, is enhanced as illustrated in panel C of FIG. 4B. According to embodiments of the present invention, enhanced sensing of near field signals improves detection and classification of arrhythmias for delivery of appropriate therapy via lead 350 and/or lead 7 from an IMD. In some embodiments according to the present invention, a second electrode 12 of lead 7 also includes a porous layer formed thereover for enhanced sensing of near-field signals within ventricle 65. As further illustrated in FIG. 4A, leads 350 and 7 may also include defibrillation electrodes 29 and 14, respectively, shown with dashed lines, for delivery of high voltage stimulation.

Figure 4B:
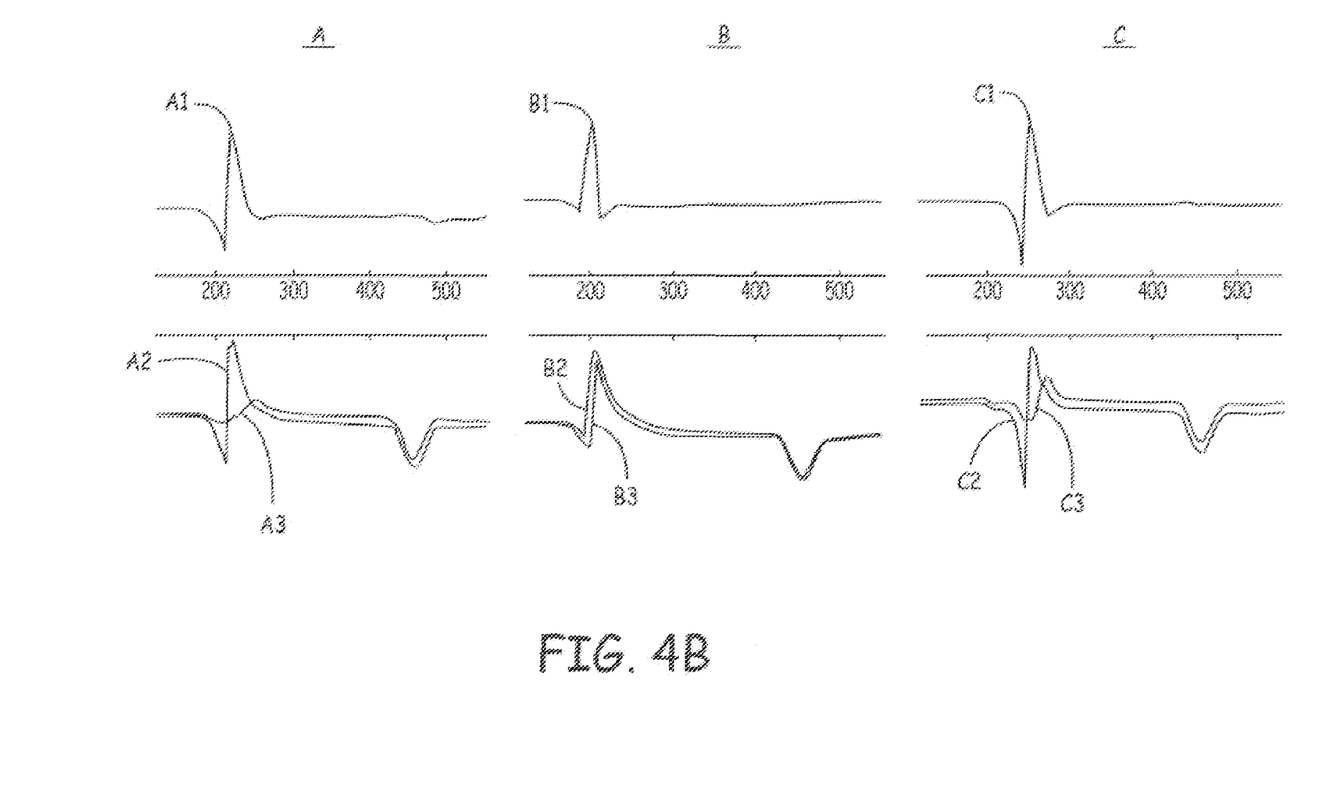
FIG. 4B is a series of signal traces illustrating function according to embodiments of the present invention.

FIG. 4B is a series of signal traces, shown in three panels, A, B and C. In each panel, the top traces, A1, B1 and C1 represent near-field signals sensed by a bipolar pair, while the bottom traces, A2, A3, B2, B3 and C2, C3 represent unipolar components of each top trace: A2, B2 and C2 are signals from a first electrode in intimate contact with tissue at an implant site, and A3, B3, and C3 are signals from a second electrode spaced proximally from the first electrode. Signal trace A1 illustrates sensing by a bipolar pair of electrodes spaced approximately 9 millimeters apart, signal trace B1 illustrates sensing by a bipolar pair of electrodes spaced approximately 4 millimeters apart and signal trace C1 illustrates sensing by a bipolar pair of electrodes spaced approximately 4 millimeters apart wherein the second electrode includes a porous layer formed thereover to prevent direct touching contact with tissue adjacent to the implant site, for example second electrode 355 illustrated in FIG. 4A, according to an embodiment of the present invention. As illustrated in FIG. 4B, signal trace C3 has a higher amplitude and slew rate than signal trace A3 but a lower amplitude and slew rate than signal trace B3, which is almost identical to B2; therefore, a combination of closer spacing between electrodes and a porous layer separating second electrode from direct touching contact with tissue adjacent to an implant site results in the largest peak-to-peak amplitude of the bipolar signal, C1, illustrated in FIG. 4B. Furthermore, according to embodiments of the present invention, prevention of direct touching contact between an anode, for example second electrodes 355 and 12 illustrated in FIG. 4A, and electrically active tissue via a porous layer prevents anodal stimulation of the tissue.

EXAMPLE

A first type of lead including a ring electrode (anode) having a porous layer formed thereover and spaced 4 millimeters from a helical tip electrode (cathode) was compared to a second type of lead including a ring electrode spaced 9 millimeters from a helical tip electrode. Two types of porous layers were employed in the first type of lead used in our study: 1.) a layer of polyurethane having a thickness of approximately 0.008 inch and a durometer of approximately 80 on a shore A scale, wherein holes, having on average a diameter of 0.001 inch, were formed by an excimer laser; and 2.) a layer of e-PTFE, obtained from Zeus (part no. 2E055-010 EO*AC), having a thickness of approximately 0.010 inch and including pores having, on average, a size between approximately 10 microns and approximately 20 microns. Both leads were implanted in a right atrial appendage of six sheep for 12 weeks. Unfiltered P-wave and far-field R-wave (FFRW) amplitudes were measured during sinus rhythm (SR) at implant, and 1, 3, 5, 8, and 12 weeks under isoflurane anesthesia. Atrial fibrillation (AF) was induced with 50 Hz rapid pacing and vagal stimulation at 12 wks, at which time, bipolar electrograms from both leads were input to an ICD atrial sense amplifier (band pass: 16 to 46 Hz), during the AF to evaluate sensing performance.

Figure 5:
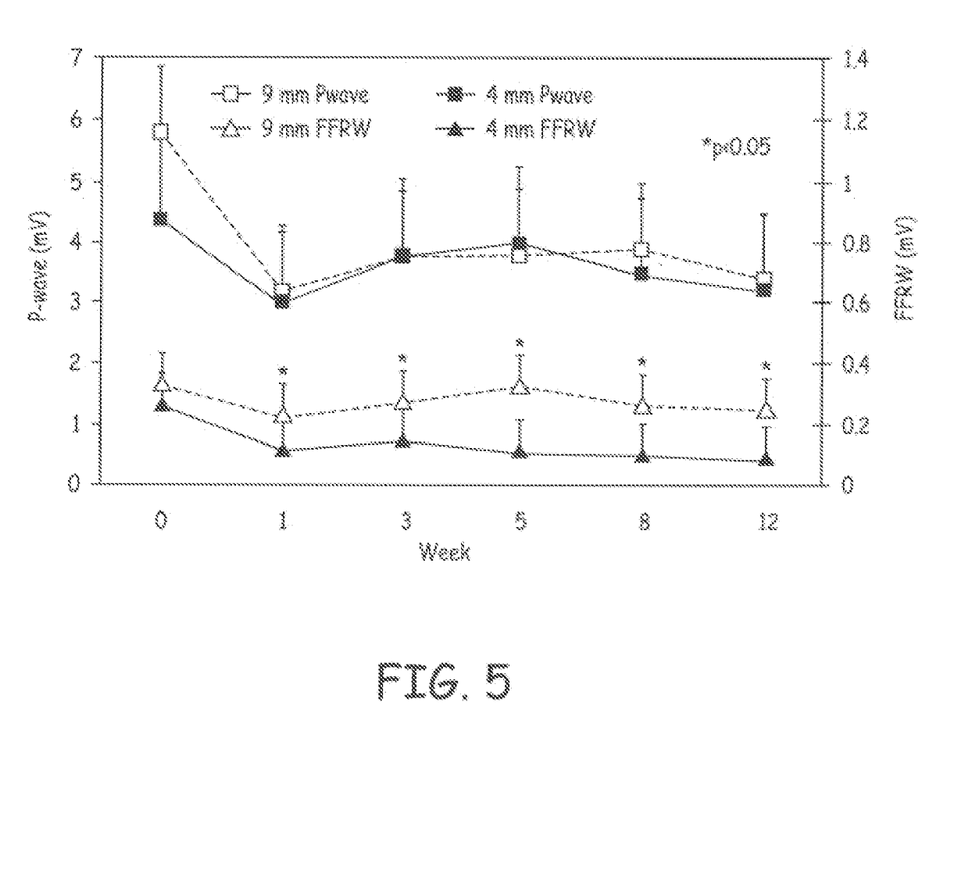
FIG. 5 is a graph illustrating results of a twelve-week animal study evaluating embodiments of the present invention.

Previous studies have shown that reducing the tip-to-ring spacing (TRS) reduces FFRW oversensing; however, short TRS has been associated with reductions in P-wave amplitude due to a close proximity of the anode to tissue adjacent to the implant site resulting in contact between the anode and active tissue. The results of our study indicate that a short TRS is feasible when the anode does not contact electrically active tissue, being separated by a porous layer. FIG. 5 presents a graph illustrating our results in which no difference was found between chronic P-wave amplitudes sensed by the second type of lead having a 9 mm TRS and the first type of lead having a 4 mm TRS, and wherein FFRW amplitudes were 50% lower as sensed by the first type of lead having the 4 mm TRS. Furthermore, our study found no difference in pacing thresholds between the second type of lead having the 9 mm TRS and the first type of lead having the 4 mm TRS and the porous layer of e-PTFE formed over the anode. Finally, no difference in sensing performance was found between unfiltered and filtered signals obtained from both types of leads compared at week 12.

While specific embodiments have been presented in the foregoing detailed description, it should be clear that a vast number of variations exist. It should also be appreciated that the exemplary embodiments are only examples, and are not intended to limit the scope, applicability, or configuration of the invention in any way. For example, a bipolar pair of electrodes according to embodiments of the present invention, although illustrated in proximity to a distal end of a lead, may be located at a position any where along a length of an implanted lead, which position is located in proximity to a target implant site. Therefore, the foregoing detailed description provides those skilled in the art with a convenient road-map for implementing an exemplary embodiment of the invention. It should be understood that various changes may be made in the function and arrangement of elements described in an exemplary embodiments without departing from the scope of the invention as set forth in the appended claims.

The invention claimed is:

1. A medical electrical lead, comprising:
    an elongated lead body including, a first elongated insulated conductor, a second elongated insulated conductor, and a connector formed at a proximal end, the connector including a first electrical contact and a second electrical contact;
    a first low voltage electrode, joined to the lead body and coupled to the first contact of the connector via the first conductor, the first electrode adapted for intimate contact with tissue at an implant site in order to provide pacing stimulation;
    a second low voltage electrode joined to the lead body in proximity to the first electrode and coupled to the second contact of the connector via the second conductor, the second electrode isolated from the first electrode and adapted to function in conjunction with the first electrode to provide bipolar sensing of near-field signals; and
    a porous layer formed over the second electrode, allowing conduction therethrough while preventing contact between the second electrode and tissue in proximity to the implant site, the porous layer comprising one of a porous silicone layer and a sheet of collagen fibers.

2. The lead of claim 1, wherein the second electrode includes an outer surface, the porous layer includes an outer surface, and the lead body includes an outer surface; the outer surface of the second electrode recessed from the outer surface of the lead body and the outer surface of the porous layer isodiametric with the outer surface of the lead body.

3. The lead of claim 1, further comprising means to promote wetting of the porous layer.

4. The lead of claim 3, wherein the means to promote wetting comprises a wetting agent applied to the porous layer.

5. The lead of claim 4, wherein the wetting agent comprises a surfactant.

6. The lead of claim 3, wherein the means to promote wetting comprises a surface treatment of the porous layer.

7. The lead of claim 1, wherein a shortest distance between the second electrode and the first electrode is between approximately 2 millimeters and approximately 9 millimeters.

8. The lead of claim 7, wherein the shortest distance is between approximately 2 millimeters and approximately 5 millimeters.

9. The lead of claim 7, wherein the shortest distance is between approximately 5 millimeters and approximately 9 millimeters.

10. The lead of claim 1, wherein the porous layer has a thickness between approximately 0.005 inch and approximately 0.020 inch.

11. The lead of claim 1, wherein the porous layer includes pores having sizes ranging, on average, between approximately 0.4 micron and approximately 50 microns.

12. The lead of claim 11, wherein the pores have sizes ranging, on average, between approximately 0.4 micron and approximately 10 microns.

13. The lead of claim 11, wherein the pores have sizes ranging, on average, between approximately 10 microns and approximately 20 microns.

14. The lead of claim 11, wherein the pores have sizes ranging, on average, between approximately 20 microns and approximately 50 microns.

15. The lead of claim 1, wherein the first electrode is positioned distal to the second electrode.

16. The lead of claim 1, wherein the first electrode includes a helix for fixation of the first electrode to the implant site.

17. The lead of claim 1, further comprising tines for fixation of the first electrode to the implant site.

18. The lead of claim 1, further comprising a high voltage electrode and wherein the lead body further includes a third insulated conductor and the connector further includes a third electrical contact; the high voltage electrode joined to the lead body, isolated from the first electrode and the second electrode, adapted for defibrillation stimulation and coupled to the third electrical contact via the third insulated conductor.

19. The lead of claim 18, wherein the high voltage electrode is positioned proximal to the second electrode.

20. The lead of claim 18, wherein the high voltage electrode is positioned distal to the first electrode.

21. The lead of claim 1, wherein the porous layer is adapted to prevent chronic tissue ingrowth.

22. A medical system, comprising:
an implantable medical device including a connector port;
an elongated lead body including, a first elongated insulated conductor, a second elongated insulated conductor, and a connector formed at a proximal end, the connector including a first electrical contact and a second electrical contact, the first electrical contact and the second electrical contact of the connector adapted to be electrically coupled to the implantable medical device within the connector port;
a first low voltage electrode joined to the lead body and coupled to the first contact of the connector via the first conductor, the first electrode adapted for intimate contact with tissue at an implant site;
a second low voltage electrode joined to the lead body in proximity to the first electrode and coupled to the second contact of the connector via the second conductor; and
a porous layer formed over the second electrode, allowing conduction therethrough while preventing contact between the second electrode and tissue in proximity to the implant site, the porous layer comprising one of a porous silicone layer and a sheet of collagen fibers;
wherein, when the connector is electrically coupled in the port of the medical device and the first electrode is contacting tissue at the implant site, the first electrode and the second electrode form a bipolar pair for stimulation of tissue at the implant site and for sensing of near-field signals in proximity to the implant site.

23. The system of claim 22, wherein a shortest distance between the first electrode and the second electrode is less than approximately 9 millimeters.

24. A medical system, comprising:
an implantable medical device including a connector port;
an elongated lead body including a distal end, a first elongated insulated conductor, a second elongated insulated conductor, and a connector formed at a proximal end, the connector including a first electrical contact and a second electrical contact, the first electrical contact and the second electrical contact of the connector adapted to be electrically coupled to the implantable medical device within the connector port;
a first low voltage electrode joined to the lead body and coupled to the first contact of the connector via the first conductor, the first electrode adapted for intimate contact with tissue at an implant site;
a second low voltage electrode joined to the lead body in proximity to the first electrode and coupled to the second contact of the connector via the second conductor; and
means for preventing the second electrode from stimulating tissue in proximity to the implant site;
wherein a minimum distance separating the second electrode from the first electrode is less than approximately 9 millimeters; and
when the connector is electrically coupled in the port of the medical device and the first electrode is contacting tissue at the implant site, the first electrode and the second electrode form a bipolar pair for stimulation of tissue at the implant site and for sensing of near-field signals in proximity to the implant site.

25. An implantable electrical medical system, comprising:
a low voltage cathode electrode assembly including a cathode surface adapted for intimate contact with electrically active tissue;
a low voltage anode electrode assembly including an anode surface and a porous layer extending over the anode surface, the porous layer comprising a sheet of collagen fibers wherein pores are formed by the collagen fibers; and
an elongate lead body to which the cathode electrode assembly and the anode electrode assembly are coupled;
wherein the anode surface is positioned in close proximity to the cathode surface for bipolar sensing of near-field electrical signals and the cathode surface and the anode surface function as a bipolar pair for pacing;
a shortest distance between the anode surface and the cathode surface is between approximately 2 millimeters and approximately 9 millimeters;
the porous collagen layer has a thickness between approximately 0.010 inch and approximately 0.020 inch and includes pores having sizes ranging, on an average, between approximately 0.4 micron and approximately 50 microns; and
the porous collagen layer extending over the anode surface allows conduction therethrough and prevents the anode surface from contacting the electrically active tissue in order to prevent anodal stimulation.

* * * * *